(12) United States Patent
Wirz (10) Patent No.: US 9,028,759 B2
(45) Date of Patent: May 12, 2015

(54) AROMA-DIFFUSING HEATING DEVICE USING A REPLACEABLE AROMA CAPSULE AND THE AROMA CAPSULE

(71) Applicant: Ming Jen Hsiao, Miaoli County (TW)

(72) Inventor: Peter Wirz, Lucerne (CH)

(73) Assignee: Ming Jen Hsiao, Miaoli County (TW)

( * ) Notice: Subject to any disclaimer, the term of this patent is extended or adjusted under 35 U.S.C. 154(b) by 0 days.

(21) Appl. No.: 14/159,249

(22) Filed: Jan. 20, 2014

(65) Prior Publication Data
US 2014/0131477 A1    May 15, 2014

Related U.S. Application Data

(63) Continuation of application No. 13/549,490, filed on Jul. 15, 2012, now Pat. No. 8,668,885.

(51) Int. Cl.
| | | |
|---|---|---|
| A62B 7/08 | (2006.01) | |
| A61L 9/00 | (2006.01) | |
| A61M 16/00 | (2006.01) | |
| A24F 25/00 | (2006.01) | |
| A61L 9/03 | (2006.01) | |

(52) U.S. Cl.
CPC ............ *A61L 9/03* (2013.01); *A61L 2209/133* (2013.01)

(58) Field of Classification Search
CPC .............. A61L 9/00; A61L 9/012; A61L 9/03
USPC ........................ 422/125, 306; 392/390; 239/44
See application file for complete search history.

(56) References Cited

U.S. PATENT DOCUMENTS

| | | |
|---|---|---|
| 3,587,968 A | 6/1971 | Hennart et al. |
| 5,647,052 A | 7/1997 | Patel et al. |
| 6,085,026 A | 7/2000 | Hammons |
| 6,413,476 B1 | 7/2002 | Barnhart |
| 6,435,563 B2 | 8/2002 | Phillips |
| D604,699 S | 11/2009 | Yamamoto |
| 8,068,725 B2 | 11/2011 | Cheung |
| 8,265,465 B2 | 9/2012 | Jorgensen |
| 8,496,881 B2 * | 7/2013 | Pohl et al. ...................... 422/125 |
| D692,548 S | 10/2013 | Wirz |
| D692,550 S | 10/2013 | Wirz |
| 8,668,885 B2 * | 3/2014 | Wirz .............................. 422/306 |

FOREIGN PATENT DOCUMENTS

| | | |
|---|---|---|
| AU | 2012101327 | 1/2013 |
| EP | 0321729 | 6/1989 |
| EP | 1473046 | 11/2004 |
| EP | 1627647 | 2/2006 |
| EP | 2067491 | 6/2009 |
| JP | 2002369705 | 12/2002 |

* cited by examiner

*Primary Examiner* — Monzer R Chorbaji
(74) *Attorney, Agent, or Firm* — Ming Chow; Sinorica, LLC (57) ABSTRACT

An aroma-diffusing heating device includes a heating base, an aroma capsule detachably accommodated in the heating base and heatable by the heating base to give off fragrance, and a cap capped on the heating base over the aroma capsule. The aroma capsule includes a heat-transfer container defining a top opening, an aromatic substance held in the heat-transfer container, and a sealing film bonded to the heat-transfer container to seal the aromatic substance in the heat-transfer container.

17 Claims, 7 Drawing Sheets

Fig. 7

AROMA-DIFFUSING HEATING DEVICE USING A REPLACEABLE AROMA CAPSULE AND THE AROMA CAPSULE

CROSS-REFERENCE

This application is a continuation of U.S. patent application Ser. No. 13/549,490 filed on Jul. 15, 2012.

FIELD OF THE INVENTION

The present invention relates to scent releasing devices and more specifically, to an aroma-diffusing heating device that uses a replaceable aroma capsule. The invention relates also to the aroma capsule.

DESCRIPTION OF THE RELATED ART

In modern society, in order to remove the smell in the air, or to enrich the spice of life, many people started using fragrance products (for example, aromatic wax, essential oils). When in use, a user needs to remove the aromatic wax from the aromatic wax container and put it in an accommodation chamber in a heater, and then electrically conduct the heater to heat the aromatic wax, causing the aromatic wax to give off fragrance.

The aforesaid application method has drawbacks. During application, the user must remove the aromatic wax from the aromatic wax container and then put the aromatic wax in the accommodation chamber in the heater carefully, avoiding direct contact of the hands with the aromatic wax. After the aromatic wax having been put in the accommodation chamber in the heater, the aromatic wax may be forced out of the heater accidentally upon an impact. Further, after the aromatic wax in the accommodation chamber in the heater is used up, the user needs to clean the accommodation chamber. If the accommodation chamber is not cleaned after each use, a new supply of aromatic wax will be mixed with the residual aromatic wax in the accommodation chamber, giving a bad smell. Further, if the accommodation chamber is formed of a fragile material (for example, ceramics), it may be broken easily during cleaning.

Therefore, it is desirable to provide an aroma-diffusing design that eliminates the drawbacks of the aforesaid prior art design.

SUMMARY OF THE INVENTION

The present invention has been accomplished under the circumstances in view. It is therefore the main object of the present invention to provide an aroma-diffusing heating device, which is configured to heat an aroma capsule to give off fragrance, wherein the aroma capsule is replaceable with a new one when used up.

To achieve this and other objects of the present invention, an aroma-diffusing heating device comprises a heating base defining a top accommodation open chamber, an aroma capsule detachably accommodated in the top accommodation open chamber of the heating base and heatable by the heating base to give off fragrance, and a cap capped on the heating base over the aroma capsule. The aroma capsule includes a heat-transfer container defining a top opening, an aromatic substance, for example, solid aromatic wax held in the heat-transfer container, and a sealing film bonded to the heat-transfer container to seal the solid aromatic wax in the heat-transfer container.

Further, the aroma capsule is configured to fit the shape of the top accommodation open chamber of the heating base.

Further, the heating base comprises a top flange raised from the top wall thereof.

Further, the heat-transfer container of the aroma capsule comprises a rim extending around the top opening. Further, the aroma capsule comprises a breathing film bonded to the heat-transfer container above the aromatic substance, for example, aromatic wax, and under the sealing film.

The invention also provides an aroma capsule for placing in a top accommodation open chamber of a heating base of an aroma-diffusing heating device and heatable by the heating base to give off fragrance. The aroma capsule comprises a heat-transfer container defining a top opening, an aromatic substance held in the heat-transfer container, a breathing film bonded to the heat-transfer container above the aromatic substance, and a sealing film bonded to the heat-transfer container to seal the aromatic material and the breathing film in the heat-transfer container.

DETAILED DESCRIPTION OF THE PREFERRED EMBODIMENT

Figure 1:
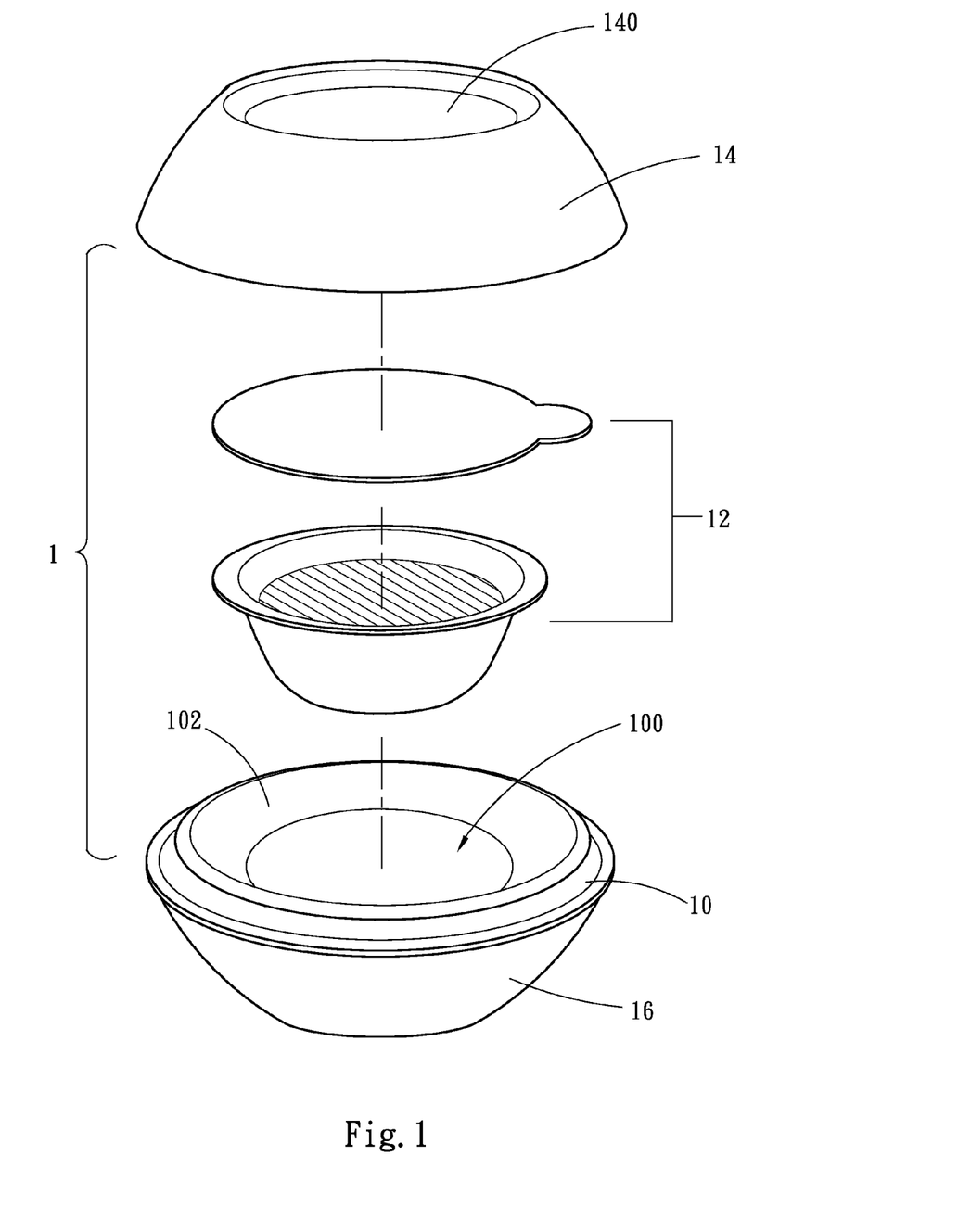
FIG. 1 is an exploded view of an aroma-diffusing heating device in accordance with the present invention.
Figure 2:
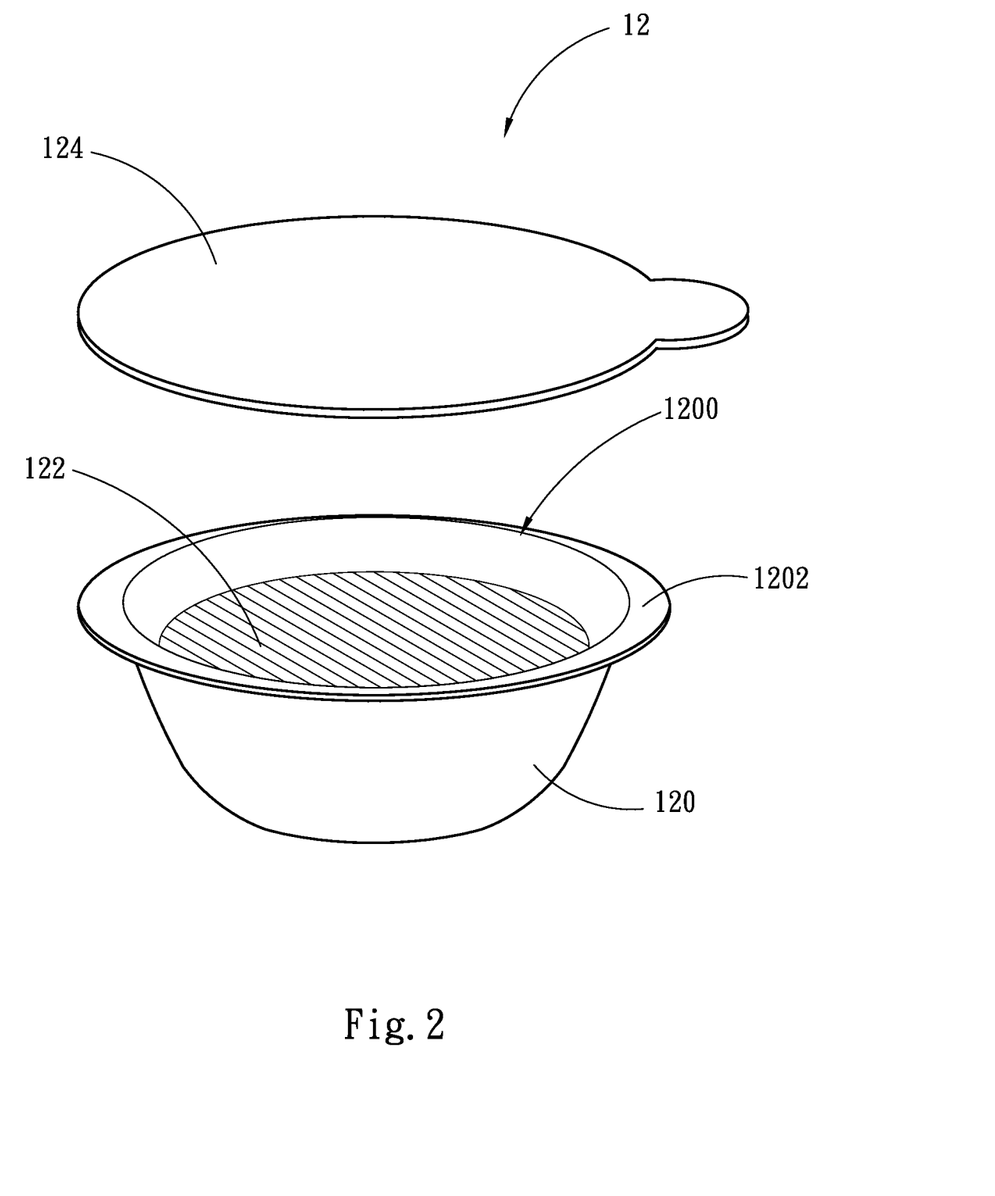
FIG. 2 is an exploded view of the aroma capsule of the aroma-diffusing heating device in accordance with the present invention.
Figure 3:
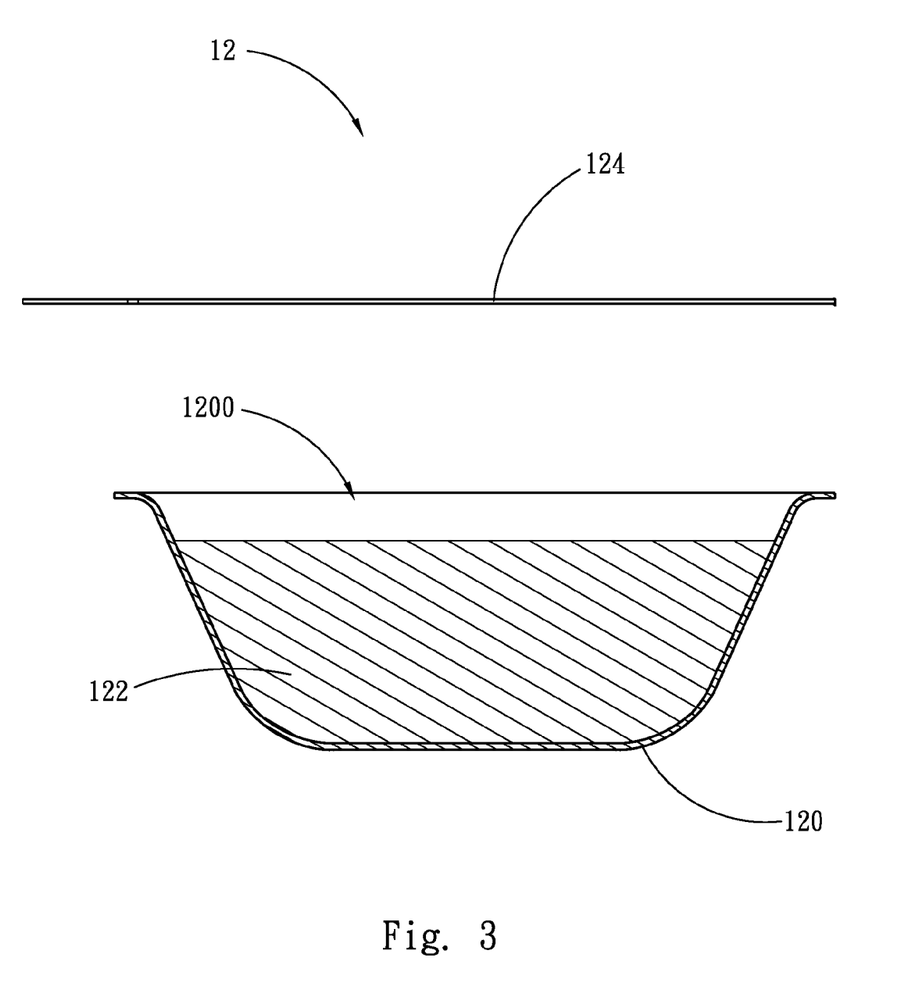
FIG. 3 is a sectional side view of FIG. 2.
Figure 4:
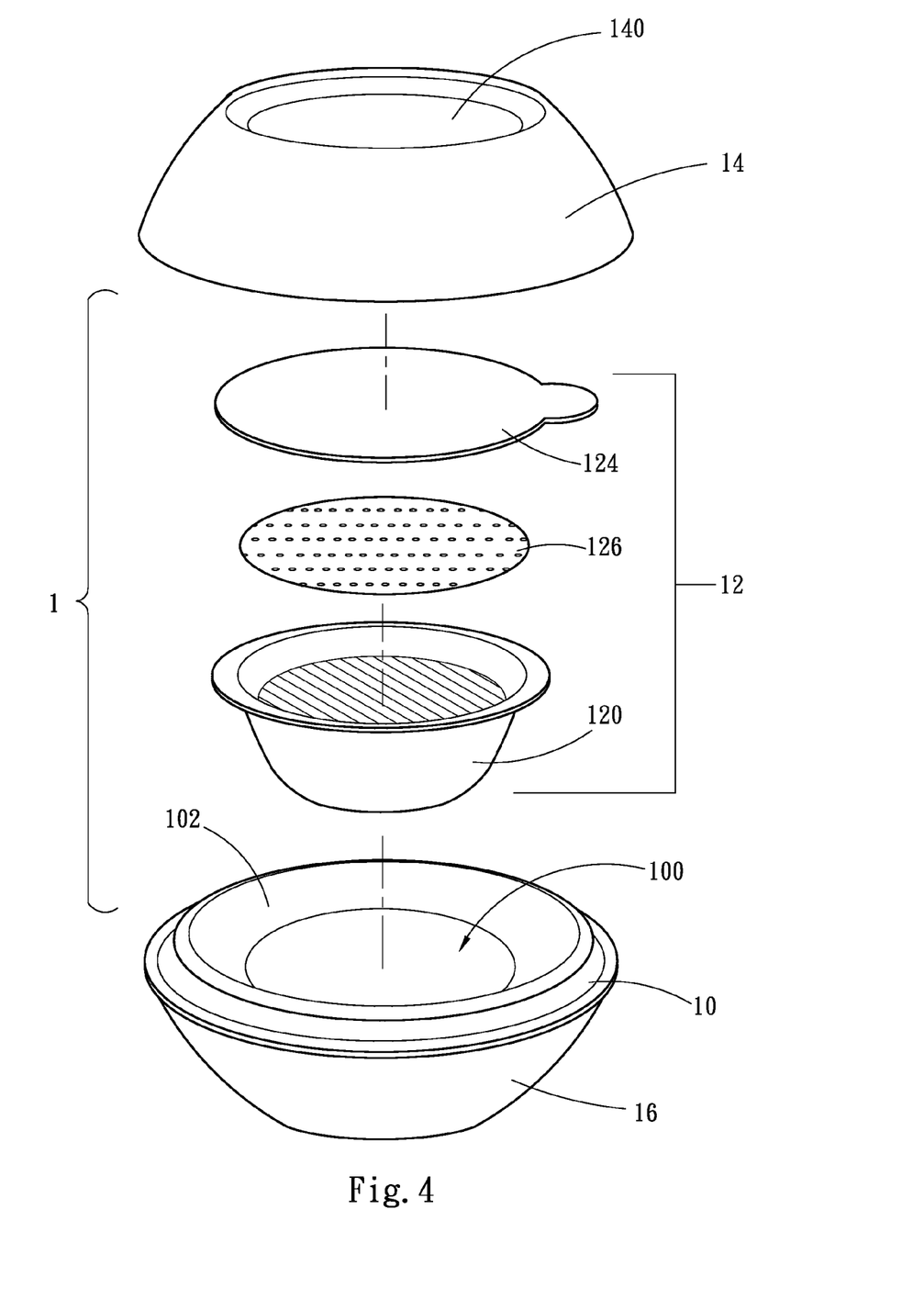
FIG. 4 is an exploded view of an alternate form of the aroma-diffusing heating device in accordance with the present invention.
Figure 5:
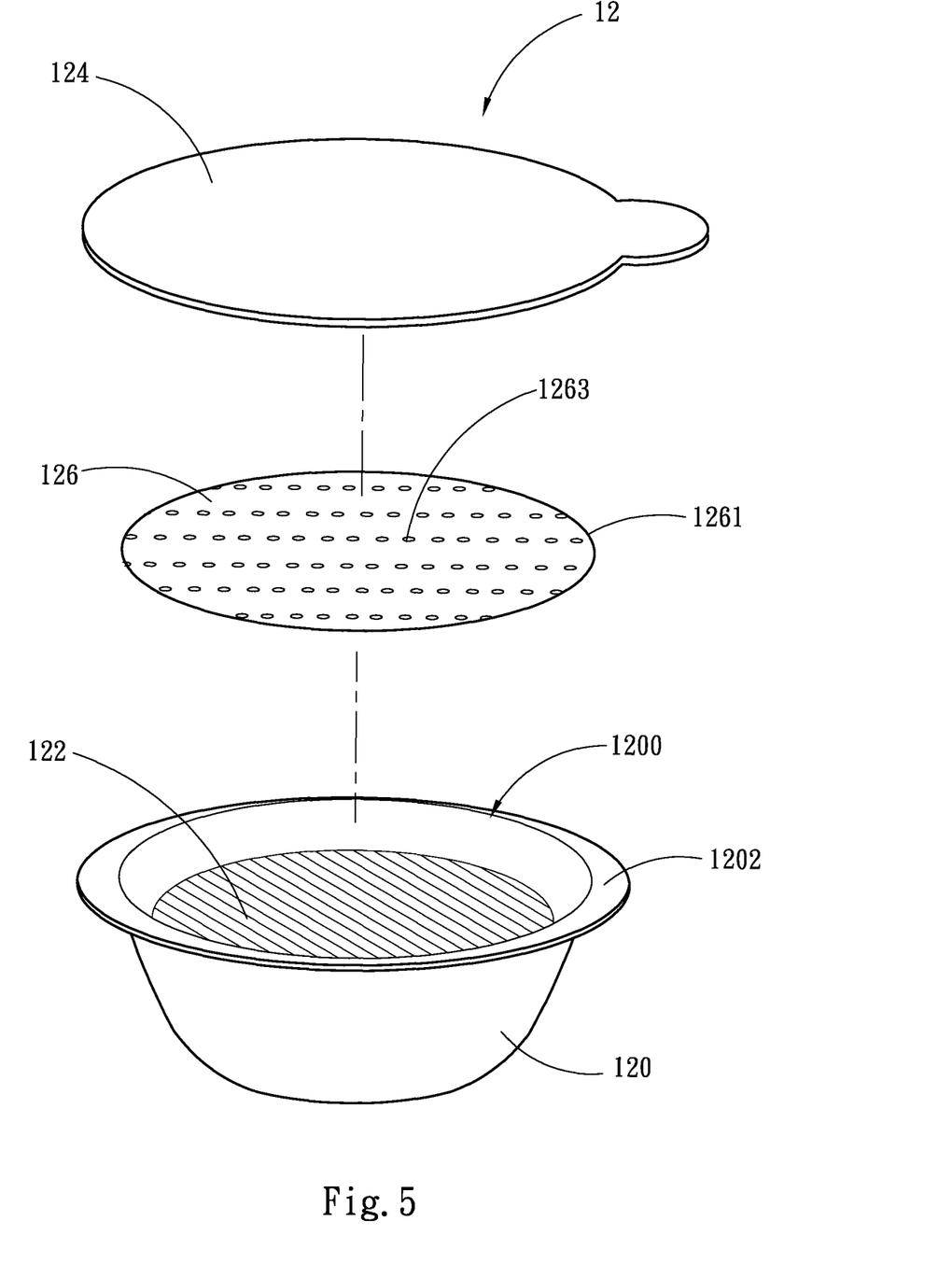
FIG. 5 is an exploded view of the aroma capsule shown in FIG. 4.
Figure 6:
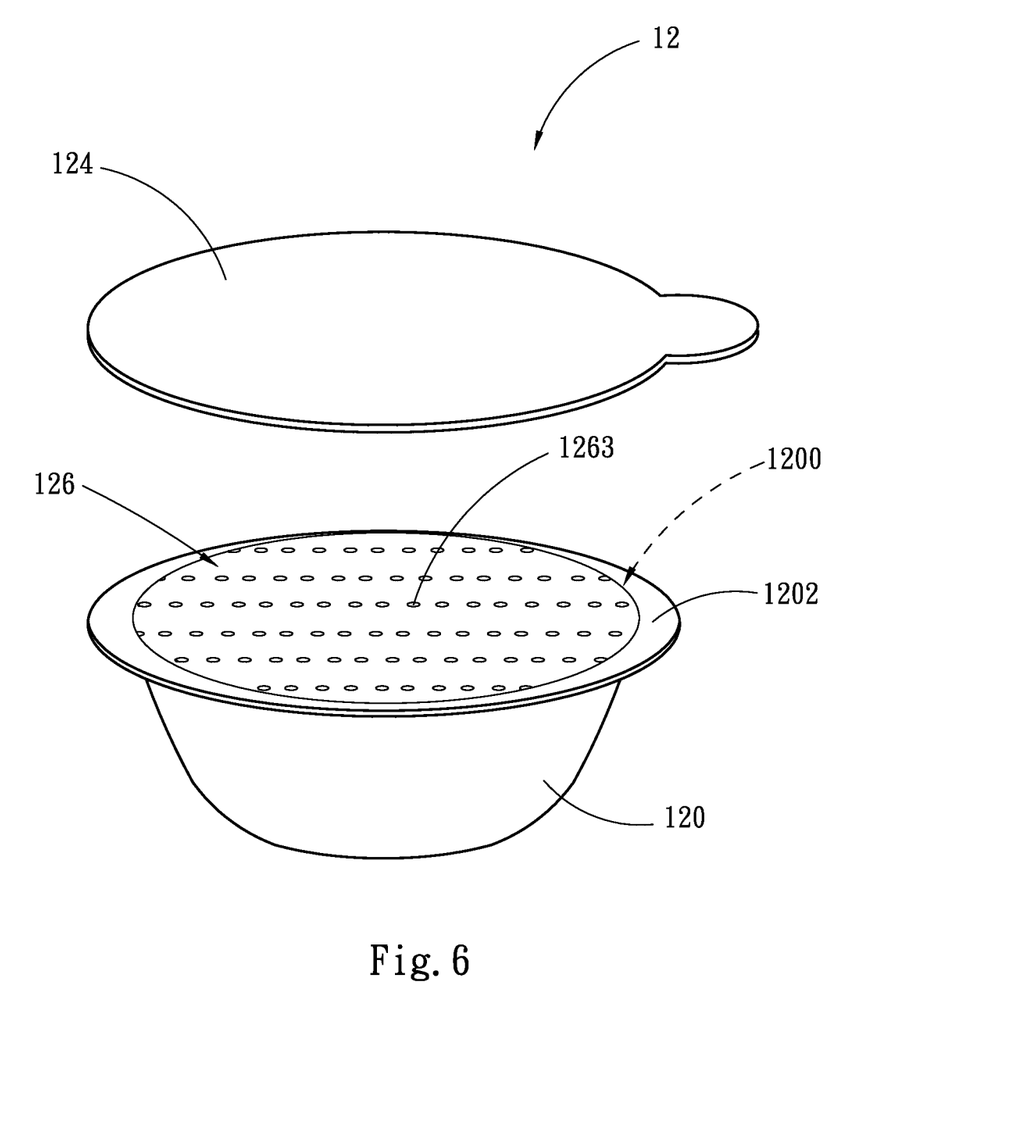
FIG. 6 corresponds to FIG. 5, illustrating the breathing film sealed to the heat-transfer container.
Figure 7:
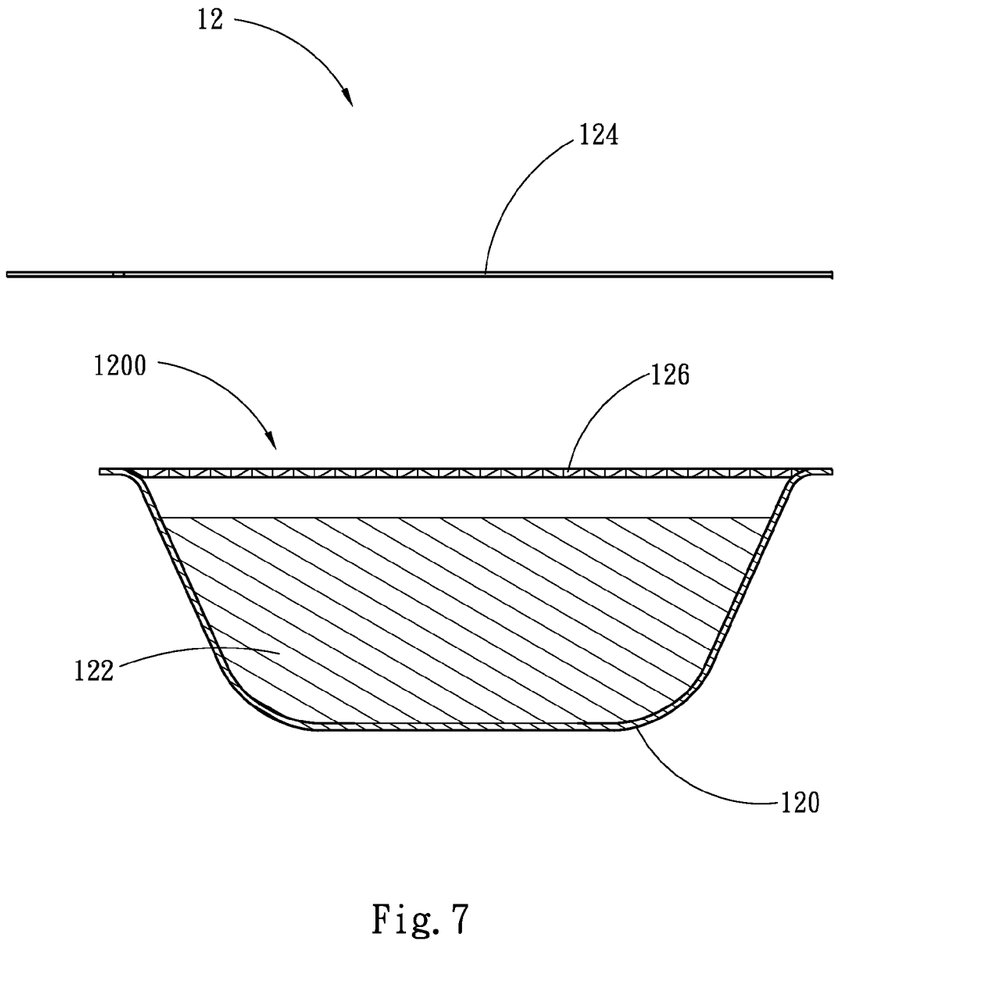
FIG. 7 is a sectional side view of FIG. 6.

Referring to FIGS. 1-3, an aroma-diffusing heating device 1 in accordance with the present invention is shown having an aroma capsule 12 therein. The aroma-diffusing heating device 1 comprises a ceramic bowl 16, a heating base 10 supported on the ceramic bowl 16 and defining a top accommodation open chamber 100 that accommodates the aroma capsule 12, and a cap 14 capped on the heating base 10 over the aroma capsule 12.

The aroma capsule 12 comprises a heat-transfer container 120 kept in contact with the heating base 10 and defining a top opening 1200, an aromatic substance 122 (for example, aromatic wax in this preferred embodiment, essential oil, or perfume) put in the heat-transfer container 120, and a sealing film 124 bonded to the heat-transfer container 120 to seal the aromatic substance 122 in the heat-transfer container 120, maintaining the quality of the aromatic substance 122.

During application, the user simply needs to remove the sealing film 124 from the rim 1202 of the heat-transfer container 120 and then electrically conducting the heating base 10 to heat the aromatic substance 122, causing the aromatic substance 122 to give off fragrance into the outside open air.

According to the present invention, the heating base 10 is configured to heat the aromatic substance 122 to about 40-70° C., or preferably 50-55° C. Within this temperature range, commercial aromatic substances can give off fragrance without destroying the quality. Further, under this temperature range of 40-70° C., the heat-transfer container 120 is maintained intact and can effectively transfer heat from the heating base 10 to the aromatic substance 122 (aromatic wax). The heat-transfer container 120 can be selected from the material group of ceramics, metals, and hard plastics. Preferably, the heat-transfer container 120 is made from a light metal, for example, aluminum foil for the advantages of light weight, high toughness and high thermal conductivity, avoiding the disadvantage of high fragileness of pottery bowls and glass containers. Further, the sealing film 124 seals the aromatic substance 122 in the top opening 1200, maintaining the quality of the aromatic substance 122.

Referring to the cross-sectional view of the aroma capsule 12 shown in FIG. 3, as stated above, the aromatic substance 122 is sealed in the aroma capsule 12 and the aroma capsule 12 is accommodated in the top accommodation open chamber 100 of the heating base 10 of the aroma-diffusing heating device 1. When using the aroma-diffusing heating device 1, the user simply needs to remove the sealing film 124 from the heat-transfer container 120 without contacting the aromatic substance 122. Further, after the aromatic substance 122 is used up, the user can put a new aroma capsule in the top accommodation open chamber 100 of the heating base 10 of the aroma-diffusing heating device 1 as a substitute and needs not to wash the heat-transfer container 120 of the used aroma capsule 12. Further, because the user does not need to clean the heat-transfer container 120, the user needs not to worry about breaking down the heat-transfer container 120. Further, the user needs not to prepare a container for holding essential oil. Further, different aroma capsules 12 designed to give off different good smells can be selectively used.

Further, the heat-transfer container 120 is configured to fit the shape of the top accommodation open chamber 100 of the heating base 10 of the aroma-diffusing heating device 1 so that the heat-transfer container 120 can be kept in close contact with the periphery of the top accommodation open chamber 100 of the heating base 10 of the aroma-diffusing heating device 1 to transfer heat energy from the heating base 10 to the aromatic substance 122 rapidly.

Further, the heating base 10 has a top flange 102 protruded from the top wall thereof around the top accommodation open chamber 100. The top flange 102 has the inside wall thereof smoothly downwardly curved toward the top accommodation open chamber 100. Thus, the user can insert the fingers along the smoothly downwardly curved inside wall of the top flange 102 to pick up the aroma capsule 12 from the top accommodation open chamber 100 conveniently. Further, the heat-transfer container 120 defines a rim 1202 around the top opening 1200. The rim 1202 can be configured to extend in a horizontal or vertical manner relative to the elevation of the top opening 1200. Thus, the user can grip the rim 1202 with the fingers to remove the aroma capsule 12 from the accommodation chamber 100 of the heating base 10 of the aroma-diffusing heating device 1 conveniently.

Further, the cap 14 defines a ventilation hole 140 for guiding fragrance out of the heat-transfer container 120 into the outside open air after removal of the sealing film 124 from the heat-transfer container 120.

FIGS. 4-7 illustrate an alternate form of the aroma-diffusing heating device 1 in accordance with the present invention. According to this alternate form, the aroma capsule 12 can be used in a wall-mount night lamp, comprising a heat-transfer container 120 defining a top opening 1200 and a rim 1202 around the top opening 1200, an aromatic substance (for example, aromatic wax) 122 held in the heat-transfer container 120, a breathing film 126 having open spaces 1263 (for example, hole) therein selected from the material group of nonwoven fabric, fiber cloth, woven fabric, porous plastic membrane and porous silicon rubber and bonded with the border edge 1261 thereof to the heat-transfer container 120 above the aromatic substance 122 (aromatic wax), and a sealing film 124 bonded to the rim 1202 of the heat-transfer container 120 to seal the aromatic substance 122 (aromatic wax) and the breathing film 126 in the heat-transfer container 120, maintaining the quality of the aromatic substance 122 (aromatic wax).

Further, the border edge 1261 of the breathing film 126 can be bonded to the inside wall of the heat-transfer container 120 in the top opening 1200. Alternatively, the border edge 1261 of the breathing film 126 can be bonded to the rim 1202 of the heat-transfer container 120 above the top opening 1200.

When compared to conventional aromatic heating devices, the aroma-diffusing heating device 1 in accordance with the present invention uses a aroma capsule 12 that can be replaced by a new one when used up, and therefore, the user needs not to prepare an extra essential oil container or to worry about breaking down the heat-transfer container, and will not touch the essential oil during replacement of the essential oil.

Although particular embodiment of the invention have been described in detail for purposes of illustration, various modifications and enhancements may be made without departing from the spirit and scope of the invention. Accordingly, the invention is not to be limited except as by the appended claims.

What the invention claimed is:

1. An aroma-diffusing heating device, comprising:
a heating base defining a top accommodation open chamber;
an aroma capsule detachably accommodated in said top accommodation open chamber and heatable by said heating base to give off fragrance;
said aroma capsule comprising a heat-transfer container accommodated in said top accommodation open chamber and kept in contact with the periphery of said top accommodation open chamber;
said heat-transfer container defining a top opening, and an aromatic substance held in said heat-transfer container;
said aroma capsule further comprises a sealing film bonded to said heat-transfer container to seal said aromatic substance in said heat-transfer container;
said heat-transfer container of said aroma capsule comprises a rim extending around said top opening; and
said sealing film is bonded to said rim of said heat-transfer container.

2. The aroma-diffusing heating device as claimed in claim 1, said aroma capsule further comprises a breathing film bonded to said heat-transfer container to keep said aromatic substance in said heat-transfer container, said breathing film having open spaces defined therein.

3. The aroma-diffusing heating device as claimed in claim 2, said breathing film has the border edge thereof bonded to said heat-transfer container in said top opening of said heat-transfer container.

4. The aroma-diffusing heating device as claimed in claim 3, said breathing film is selected from the material group of nonwoven fabric, fiber cloth, woven fabric, porous plastic membrane or porous silicon rubber.

5. The aroma-diffusing heating device as claimed in claim 1, said heating base comprises a top flange raised from a top wall thereof around said top accommodation open chamber, said top flange having an inside wall thereof smoothly downwardly curved toward said top accommodation open chamber.

6. The aroma-diffusing heating device as claimed in claim 1, wherein said aromatic substance is a aromatic wax.

7. The aroma-diffusing heating device as claimed in claim 1, further comprising:
a cap capped on said heating base over said aroma capsule.

8. An aroma capsule for placing in a top accommodation open chamber of a heating base of an aroma-diffusing heating device and heatable by said heating base to give off fragrance, comprising:
a heat-transfer container defining a top opening and a rim around said top opening;
an aromatic substance held in said heat-transfer container;
a sealing film bonded to said rim of said heat-transfer container to seal said aromatic substance in said heat-transfer container; and
said aromatic substance is a aromatic wax.

9. The aroma capsule as claimed in claim 8, further comprising a breathing film bonded to said heat-transfer container above said aromatic substance in said heat-transfer container and under said sealing film, said breathing film having open spaces defined therein.

10. The aroma capsule as claimed in claim 8, wherein said breathing film has the border edge thereof bonded to said heat-transfer container in said top opening of said heat-transfer container.

11. An aroma capsule comprising:
a heat-transfer container defining a top opening;
an aromatic substance held in said heat-transfer container;
a breathing film bonded to said heat-transfer container above said aromatic substance in said heat-transfer container, said breathing film having open spaces defined therein; and
said breathing film bonded to said heat-transfer container in said top opening of said heat-transfer container.

12. The aroma capsule as claimed in claim 11, said aroma capsule further comprises a sealing film bonded to said heat-transfer container to seal said aromatic substance in said heat-transfer container and said breathing film under said sealing film.

13. The aroma capsule as claimed in claim 11, said heat-transfer container of said aroma capsule comprises a rim extending around said top opening; said breathing film is bonded to said rim of said heat-transfer container.

14. The aroma capsule as claimed in claim 13, wherein said breathing film has the border edge thereof bonded to said heat-transfer container in said rim of top opening of said heat-transfer container.

15. The aroma capsule as claimed in claim 14, said aroma capsule further comprises a sealing film bonded to said heat-transfer container to seal said aromatic substance in said heat-transfer container and said breathing film under said sealing film.

16. The aroma capsule as claimed in claim 11 wherein said breathing film has the border edge thereof bonded to said heat-transfer container in said top opening of said heat-transfer container.

17. The aroma capsule as claimed in claim 11 wherein said aromatic substance is an aromatic wax.

* * * * *